(12) United States Patent
Fischer et al.

(10) Patent No.: US 7,749,271 B2
(45) Date of Patent: Jul. 6, 2010

(54) SURGICAL GUIDING INSTRUMENT

(75) Inventors: Kay Fischer, Tuttlingen (DE); Robert Schultz, Tuttlingen (DE)

(73) Assignee: Aesculap AG & Co KG, Tuttlingen (DE)

( * ) Notice: Subject to any disclaimer, the term of this patent is extended or adjusted under 35 U.S.C. 154(b) by 881 days.

(21) Appl. No.: 11/508,461

(22) Filed: Aug. 23, 2006

(65) Prior Publication Data

US 2007/0118145 A1    May 24, 2007

(30) Foreign Application Priority Data

Nov. 24, 2005   (DE) ........................ 10 2005 056 824

(51) Int. Cl.
*A61F 2/00* (2006.01)
*A61B 17/60* (2006.01)
*A61B 17/00* (2006.01)
*A61B 17/58* (2006.01)

(52) U.S. Cl. ........................ 623/17.11; 606/79; 606/99; 606/914

(58) Field of Classification Search ............... 606/79, 606/86 R, 90, 99, 86 A, 914; 623/17.11–17.16
See application file for complete search history.

(56) References Cited

U.S. PATENT DOCUMENTS

| | | | |
|---|---|---|---|
| 7,491,204 B2 * | 2/2009 | Marnay et al. ............ 606/86 R |
| 7,547,308 B2 * | 6/2009 | Bertagnoli et al. ............ 606/90 |
| 2004/0215198 A1 | 10/2004 | Marnay et al. |
| 2005/0113842 A1 * | 5/2005 | Bertagnoli et al. ............ 606/90 |
| 2007/0260320 A1 * | 11/2007 | Peterman et al. ......... 623/17.16 |
| 2008/0097452 A1 * | 4/2008 | Assell et al. .................. 606/90 |
| 2009/0216330 A1 * | 8/2009 | Geisert et al. ............ 623/17.16 |

FOREIGN PATENT DOCUMENTS

| | | |
|---|---|---|
| DE | 10340150 | 3/2005 |
| WO | WO 03/092507 | 11/2003 |
| WO | WO 2005/020859 | 3/2005 |

OTHER PUBLICATIONS

Brochure, "Aesculap Spine active L—operating technique" (available to public after Nov. 24, 2005).
Brochure "Aesculap Spine active L—Generation: active, rotation+translation=mobilization" (available to public after Nov. 24, 2005).

* cited by examiner

*Primary Examiner*—Eduardo C Robert
*Assistant Examiner*—Ellen C. Hammond
(74) *Attorney, Agent, or Firm*—RatnerPrestia (57) ABSTRACT

A surgical guiding instrument for use with a chisel and an implant body for insertion into an intervertebral space, included is a shaft with a stop device for delimiting a depth of insertion of the implant body into the intervertebral space. The shaft has a distal end and a proximal end, the implant body being arranged at the distal end of the shaft and defining two bearing surfaces positionable against the adjacent vertebral bodies, the stop device having at least one stop movably mounted at the distal end of the shaft or on the implant body, the stop having a stop surface pointing in distal direction transversely or substantially transversely to at least one of the bearing surfaces, so that an insertion depth for a surgical machining tool can be set in a simple way.

49 Claims, 4 Drawing Sheets

SURGICAL GUIDING INSTRUMENT

This application claims priority to German Application No. 10 2005 056 824.6, filed Nov. 24, 2005, which is incorporated herein by reference in its entirety.

BACKGROUND OF THE INVENTION

The present invention relates to a surgical guiding instrument for a surgical machining tool, in particular, a chisel, with an implant body for insertion into an intervertebral space between adjacent vertebral bodies of the vertebral column of a human being or an animal, with a shaft and with a stop device for delimiting a depth of insertion of the implant body into the intervertebral space, the shaft having a distal end and a proximal end, the implant body being arranged at the distal end of the shaft and defining two bearing surfaces positionable against the adjacent vertebral bodies, the stop device having at least one stop movably mounted at the distal end of the shaft or on the implant body, the stop having a stop surface pointing in distal direction transversely or substantially transversely to at least one of the bearing surfaces.

Degenerative processes in the intervertebral disks articulatedly joining adjacent vertebral bodies of the vertebral column to one another are often the cause of disorders in the area of the vertebral column. In cases where the intervertebral disks have become so degenerated that they are no longer maintainable, they are often replaced by artificial intervertebral disks, so-called intervertebral implants. These can join adjacent vertebral bodies to one another rigidly or articulatedly, depending on the design of the intervertebral implant. Such intervertebral implants are often provided with fin-like projections which extend from bearing surfaces designed to bear against vertebral body surfaces adjoining the intervertebral space and prevent relative movement between the intervertebral implant and the vertebral bodies against which they bear. When introducing the intervertebral implant comprising one or two or more fin-like projections into the intervertebral space, in order to prevent damage, for example, by splitting the respective vertebral body, there are formed, for example, milled or cut with a chisel, on the vertebral bodies, prior to insertion of the intervertebral implant, grooves with which the fin-like projections of the intervertebral implant can engage. When doing so, a problem arises with the machining tool, for example, a chisel or a milling tool, being advanced ventrally too far into the intervertebral space in the direction towards the spinal canal of the spinal column. In order to avoid this, instruments are known, which comprise a stop for preventing the guiding instrument from being introduced too far into the intervertebral space, so that an insertion or cutting depth of a machining tool is delimited, more specifically, by the stop device of the instrument.

The stop devices of known instruments are arranged directly at a distal end of the instrument and can only be adjusted before the implant body of the guiding instrument is inserted into the intervertebral space. In order to vary an insertion depth or cutting depth of the surgical machining tool, the guiding instrument must be removed each time from the patient's body. Alternatively, an access to the body, which is of such size as to permit adjustment of the stop device, must be created. Minimally invasive surgery would then be virtually impossible.

The object underlying the present invention is, therefore, to so improve a surgical guiding instrument of the kind described at the outset that an insertion depth for a surgical machining tool can be set in a simple way.

SUMMARY OF THE INVENTION

This object is accomplished with a surgical guiding instrument of the kind described at the outset, in accordance with the invention, in that the stop device comprises an actuating member arranged at the proximal end or in the region of the proximal end of the shaft and a power transmission member mounted on the shaft, and in that the actuating member, the power transmission member and the at least one stop are arranged and designed to interact in such a way that the at least one stop is movable in proximal and/or distal direction by actuating the actuating member.

The further development according to the invention has the advantage that the preparation of the vertebral bodies prior to insertion of an intervertebral implant with fin-like projections is considerably simplified. In particular, the guiding instrument can be inserted, more specifically, through a minimally invasive access, and, after insertion, the stop device can be actuated by the actuating member from outside the body of the human being or animal, in order to adjust the stop. Accordingly, a maximum insertion depth of a surgical machining tool can also be optionally altered by altering the relative position between stop and implant body of the guiding instrument. This can be done with, for example, the assistance of X-ray monitoring, so as to ensure that when machining the vertebral bodies adjoining the intervertebral space only as much material is removed from the respective vertebral body as is actually required for insertion of the intervertebral implant. In addition, when preparing the vertebral bodies, the machining tool is thereby prevented from entering the spinal canal and causing injury.

It is advantageous for the actuating member to be releasably connectable to the power transmission member. This allows the guiding instrument to be disassembled also for cleaning purposes. Furthermore, the actuating member can thus also be removed and, for example, replaced by another instrument.

It is also conceivable to provide an actuating member to which several different guiding instruments are connectable.

It is expedient for a coupling device to be provided for connecting the power transmission member to the actuating member, for a first coupling member and a second coupling member engageable in a coupling position with the first coupling member to be provided, for the first coupling member to be arranged on the actuating member, and for the second coupling member to be arranged on the power transmission member. This further development makes it possible for the actuating member to be connected in a simple way to the power transmission member.

It may be advantageous for one of the two coupling members to be a member of polygonal cross section having outer planar sides or a member of generally polygonal cross section having outer rounded sides and edges, and for the other one of the two coupling members to be a corresponding member of polygonal cross section having inner planar sides or a corresponding member of generally polygonal cross section having inner rounded sides and edges. This enables a connection between the actuating member and the power transmission member with positive and/or force locking, so that a movement of the actuating member reliably results in a corresponding movement of the power transmission member. For example, the power transmission member can be mounted for displacement and/or rotation on the shaft.

For easy handling of the guiding instrument, it is expedient for a handle part to be provided at the proximal end of the shaft.

It is advantageous for the handle part to be releasably connectable to the shaft. This has, in particular, the advantage that when not required, for example, whenever the implant body is inserted in a desired manner in the intervertebral space, the handle part can be removed so as not to interfere at the operating site. Moreover, this also has the advantage that a handle part can be provided for different shafts. This means that, for example, in an operating theater only a single handle part is required, and that a set of different shafts with different implant bodies can be provided, so that individual guiding instruments can be selected in dependence upon the size of the intervertebral implant to be inserted.

It is particularly easy to connect the shaft to the handle part when a connecting device is provided for connecting the shaft to the handle part, when a first connecting member and a second connecting member engageable in a connecting position with the first connecting member are provided, when the first connecting member is arranged on the shaft, and when the second connecting member is arranged on the handle part.

A connection between the shaft and the handle part with positive locking and/or force locking is achievable in a simple way when one of the two connecting members is a member of polygonal cross section having outer planar sides or a member of generally polygonal cross section having outer rounded sides and edges, and when the other one of the two connecting members is a corresponding member of polygonal cross section having inner planar sides or a corresponding member of generally polygonal cross section having inner rounded sides and edges.

In particular, it may be expedient for the member of polygonal cross section having outer planar sides to form a short shaft section of the shaft, and for the member of polygonal cross section having inner planar sides to be arranged on the handle part. This makes it possible for the shaft to be partially introducible, for example, with its proximal end, into the handle part. The member of polygonal cross section having inner planar sides thus forms a shaft receptacle for the member of polygonal cross section having outer planar sides.

To enable the handle part and the shaft to be separated from one another in a simple way, it is expedient for the connecting device to be designed in the form of a locking connection, for example, a snap-in connection, for the two connecting members to be designed in the form of locking members which in a lock position are engaged, and for the two locking members to be arranged so that they are movable relative to one another during the transition from the lock position to a release position in which they are disengaged, and vice versa. With such a locking connection, for example, the shaft and the handle part can be assembled in a simple way. To release the locking connection, the two locking members in engagement in the lock position need only be moved relative to one another in such a way as to disengage. The shaft and the handle part can then be moved relative to one another and separated from one another.

It is advantageous for one of the locking members to be designed in the form of a locking recess arranged on the shaft, and for the other locking member to be a spring-biased locking latch mounted on the handle part. It is, of course, also possible for the two locking members to be arranged conversely on the shaft and the handle part. The proposed design does, however, have the advantage that the shaft is particularly easy to design and particularly easy to manufacture, so that, in particular, also only one handle part need be provided for different shafts, which results in a considerable reduction of costs for the manufacture of a set of different guiding instruments.

In order to safely prevent the shaft from becoming unintentionally detached from the handle part, it is advantageous for the locking latch to be mounted for movement in a direction transverse to the longitudinal axis of the shaft. Thus, forces acting on the guiding instrument in the direction of the longitudinal axis of the shaft cannot result in the handle part becoming detached from the shaft.

In principal, it is conceivable to arrange the actuating member on the shaft. In a set of different guiding instruments, an actuating member would then also have to be provided on each shaft. It is, therefore, advantageous for the actuating member to be arranged on the handle part. Provision of an actuating member on each shaft can thereby be dispensed with. If the handle part is detachable from the shaft, then the actuating member can also be detached from the shaft and from the power transmission member.

It is conceivable for the power transmission member to be mounted on the shaft for displacement in the direction of the longitudinal axis thereof. It is expedient for the power transmission member to be a drive shaft mounted for rotation on the shaft. Movement of the power transmission member and the shaft relative to one another in the direction of the longitudinal axis is thereby prevented. In particular, the rotatably mounted drive shaft is suitable for being made to rotate by the actuating member and for moving the at least one stop directly or indirectly.

It is conceivable to provide the actuating member as a push-and-pull member displaceable parallel to the longitudinal axis of the shaft. It is, however, particularly expedient for the actuating member to be a drive wheel mounted for rotation about a longitudinal axis of the shaft. As a result, it can be connected in a simple way to a power transmission member rotatably mounted on the shaft. In addition, it can be actuated particularly easily and ergonomically, as rotation of the actuating member does not require any forces to act in the direction of the longitudinal axis on the guiding instrument, which might result in a change in the position thereof.

A chisel guide is preferably provided on the implant body. This may serve for introduction of a chisel or another machining tool, with which a vertebral body can be machined, in particular, partly resected.

A particularly simple design of the guiding instrument is obtained when the chisel guide comprises at least one guide groove and when the at least one guide groove is arranged so as to run in one of the two bearing surfaces parallel or substantially parallel to the longitudinal axis. A machining tool, for example, a chisel, can thus be guided in a simple way in the guide groove so as to resect part of a vertebral body for formation of a recess for receiving a fin-like projection on an intervertebral implant.

Optimum guidance along as long a distance as possible is obtained by at least part of the chisel guide projecting at the proximal end from the implant body. The proximally projecting part may simultaneously serve as stop for the machining tool when it is moved in the chisel guide relative to the implant body.

In order that, in particular, a double chisel with two blades may be used as machining tool for simultaneously preparing a receptacle for a guide projection on the intervertebral implant on each of the two vertebral bodies adjoining the intervertebral space, it is advantageous for the chisel guide to respectively comprise a longitudinal groove on each bearing surface.

In accordance with a preferred embodiment of the invention, it can be provided that the at least one stop is mounted on the implant body for displacement parallel or substantially parallel to the longitudinal axis. It is thus possible to change a position of the implant body relative to the vertebral bodies adjoining the intervertebral space parallel or substantially parallel to the longitudinal axis.

To enable the stop to be moved in a simple way, it is expedient, for a drive mechanism to be provided for moving the at least one stop, and for the drive mechanism to be arranged on the shaft or on the implant body and designed so that the at least one stop is movable as a result of a movement of the power transmission member. For example, the drive mechanism can be provided in such a way that the stop is movable as a result of a translational and/or a rotational movement of the power transmission member. The drive mechanism thus makes it possible to move the stop only by moving the power transmission member, for example, also via the actuating member.

A particularly simple design of the guiding instrument is obtained when the drive mechanism comprises a spindle drive for moving the at least one stop.

It is expedient for the spindle drive to comprise a bearing slide mounted on the implant body for displacement parallel or substantially parallel to the longitudinal axis and carrying the at least one stop, and a threaded spindle mounted for rotation about an axis of rotation extending parallel or substantially parallel to the longitudinal axis and having an outer thread corresponding to an inner thread provided on the bearing slide, and for the threaded spindle to be connected or connectable to the power transmission member. A spindle drive of such design makes it possible, as a result of rotation of the power transmission member, to rotate the threaded spindle and thereby bring about a movement of the bearing slide parallel or substantially parallel to the longitudinal axis. The at least one stop can thereby be moved in a desired manner.

The at least one stop preferably projects transversely to the longitudinal axis from a proximal end of the bearing slide. In this way it is possible for the stop to come into contact with the vertebral bodies adjoining the intervertebral space and thus delimit an insertion depth of the implant body into the intervertebral space.

In order that the guiding instrument can be disassembled in a simple way, it is advantageous for the drive mechanism to comprise a power transmission member receptacle with which a distal end of the power transmission member engages in a positively locked manner. This also facilitates manufacture, in particular, assembly and cleaning, of the instrument.

In principal, it is possible for the at least one stop member to be mounted so as to project in distal direction from the implant body. However, insertion of the implant body into the intervertebral space is thereby made difficult. It is, therefore, expedient for the at least one stop to be mounted so as to project in proximal direction from the implant body. The implant body can thus be pushed into the intervertebral space until the at least one stop bears against the vertebral bodies adjoining the intervertebral space.

In order that as low forces as possible will act on the adjacent vertebral bodies when the at least one stop bears against these in order to delimit an insertion depth of the implant body into the intervertebral space, it is advantageous for two or four stops to be provided. Damage to the vertebral bodies in an undesirable manner is thereby avoided.

The design of the guiding instrument is particularly simple when it is of mirror-symmetrical design in relation to a mirror plane containing the longitudinal axis. It can, for example, also be of symmetrical design in relation to two mirror planes extending perpendicularly to one another.

The object stated at the outset is also accomplished by a set of surgical guiding instruments for a surgical machining tool, with an implant body for insertion into an intervertebral space between adjacent vertebral bodies of the vertebral column of a human being or an animal, with a shaft and with a stop device for delimiting a depth of insertion of the implant body into the intervertebral space, the shaft having a distal end and a proximal end, the implant body being arranged at the distal end of the shaft and defining two bearing surfaces positionable against the adjacent vertebral bodies, the set comprising two or more of the above-described guiding instruments, and the two or more guiding instruments comprising implant bodies of different size and/or different shape. With such a set it is possible to respectively select for a surgical procedure that guiding instrument which is optimally suited in shape and size for insertion into the intervertebral space before machining the vertebral body surfaces with the machining tool.

Since the implant body is, in particular, selected so as to fill out the intervertebral space in such a way that a spacing between the adjacent vertebral bodies corresponds, also during the surgical procedure, to the original spacing between these, it is expedient for the implant bodies to have different thicknesses and/or different angles of inclination between the bearing surfaces. Injury to the vertebral column, in particular, to the vertebral bodies adjoining the intervertebral space, is thereby avoided.

The object stated at the outset is also accomplished, in accordance with the invention, by a surgical instrumentarium comprising at least one surgical machining tool, in particular, a chisel, and at least one surgical guiding instrument for the at least one surgical machining tool, with an implant body for insertion into an intervertebral space between adjacent vertebral bodies of the vertebral column of a human being or an animal, with a shaft and with a stop device for delimiting a depth of insertion of the guiding instrument into the intervertebral space, the shaft having a distal end and a proximal end, the implant body being arranged at the distal end of the shaft and defining two bearing surfaces positionable against the adjacent vertebral bodies, the stop device having at least one stop movably mounted at the distal end of the shaft or on the implant body, the stop having a stop surface pointing in distal direction transversely or substantially transversely to at least one of the bearing surfaces, the at least one surgical guiding instrument being one of the above-described guiding instruments or one of the above-described sets of guiding instruments.

The instrumentarium according to the invention is exceedingly well suited for providing vertebral bodies with receptacles in which a projection on an intervertebral implant can engage. In particular, with the instrumentarium, the machining tool can be prevented from being introduced too deeply in anterior/posterior direction into the intervertebral space.

In principal, it is conceivable for the at least one machining tool to be a milling tool for milling a groove or a recess in a vertebral body. However, the at least one machining tool is preferably a single or a double chisel. A groove can be formed with this in a simple way in the respective vertebral body.

It is expedient for the at least one machining tool to comprise a hollow tool shaft, at the distal end of which at least one tool cutting edge is arranged, and for the shaft of the guiding instrument to be introducible into the tool shaft. In the case of a guiding instrument, for example, in which the handle part can be separated from the shaft, it is possible, after inserting the implant body into the intervertebral space, for example, for the handle part to be removed and the machining tool to be pushed forward with its tool shaft over the shaft of the guiding instrument. The machining tool is thereby additionally guided on the guiding instrument.

The object stated at the outset is also accomplished, in accordance with the invention, by a method for preparing an intervertebral space for inserting an intervertebral implant with two implant bearing surfaces essentially pointing away from one another and designed to bear against vertebral body surfaces, adjoining the intervertebral space, of adjacent vertebral bodies of the vertebral column of a human being or an animal, the implant bearing surfaces having at least one fin-like projection extending transversely or substantially transversely from at least one implant bearing surface, wherein the intervertebral space is cleared out, wherein a surgical guiding instrument with an implant body, a guide for a machining tool and a stop device comprising at least one stop is used, wherein the at least one stop is adjusted so that the implant body is only insertable to a minimum depth into the intervertebral space, wherein the implant body is inserted into the intervertebral space until the at least one stop bears against the adjacent vertebral bodies, wherein the at least one stop is adjusted in dependence upon a desired depth of the tool relative to the implant body, and the implant body is advanced further into the intervertebral space until the at least one stop bears against the adjacent vertebral bodies again, and wherein at least one recess is formed in at least one of the two adjacent vertebral bodies with the machining tool guided in the guide.

The method according to the invention ensures that the recess is machined in at least one vertebral body in such a way that, beyond that, there will be no damage caused to the vertebral body or injury to the vertebral column, for example, to the spinal canal. A chisel guided in the guide may, for example, be used as machining tool for forming the recess in the vertebral body.

One of the above-described guiding instruments is advantageously used as guiding instrument. Performance of the method with such a guiding instrument has the advantage that unintentional injury to the vertebral column by the surgical procedure is prevented.

To prevent the machining tool from being advanced too far into the vertebral body, it is advantageous for the at least one stop to be adjusted with the assistance of X-ray monitoring. It is thereby ensured that neither the implant body nor the machining tool guided in the guide can injure the vertebral column in an undesirable manner.

It is also expedient for one of the above-described instrumentaria to be used.

In order to ensure, when preparing the at least one vertebral body, that the intervertebral implant to be inserted can be optimally fitted into the intervertebral space, it is advantageous for a guiding instrument with an implant body to be selected, and for a height of the implant body and an angle between the implant bearing surfaces of the implant body to correspond to a height and an angle of an implant for implantation. Accordingly, when an operator has decided which implant is to be inserted into the intervertebral space, he can select the corresponding guiding instrument. In particular, this has the advantage that he can form the recess in the respective vertebral body with the machining tool without any further deliberation and without fear of any undesirable injury to the vertebral column.

The following description of a preferred embodiment of the invention serves to explain the invention in greater detail in conjunction with the drawings.

DETAILED DESCRIPTION OF THE INVENTION

Figure 1:
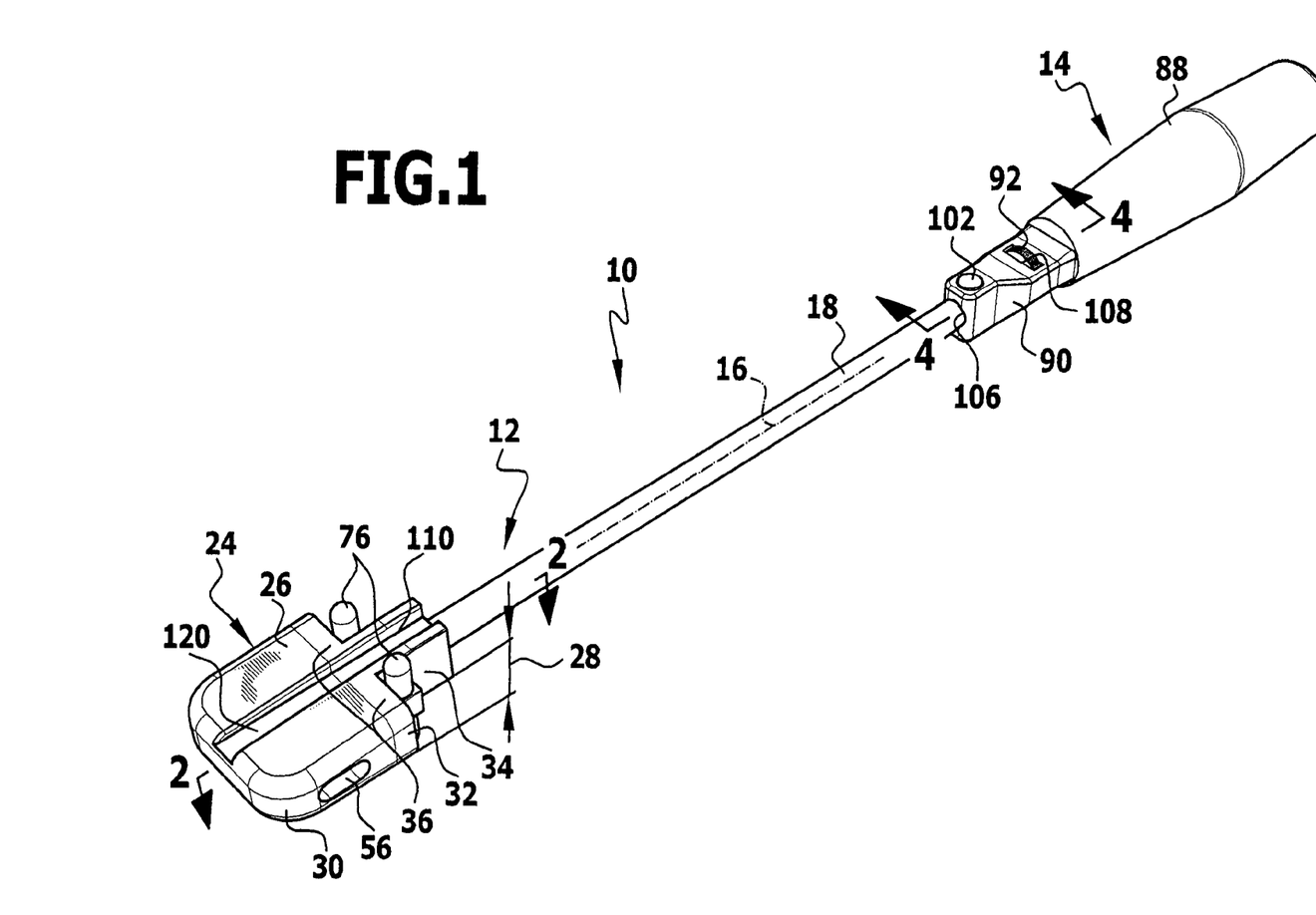
FIG. 1 shows a perspective illustration of a guiding instrument according to the invention.

FIG. 1 shows a surgical guiding instrument, generally designated by reference numeral 10, which essentially comprises two parts, namely a shaft part 12 and a handle part 14, which are releasably connectable to one another.

The shaft part 12 comprises an elongated hollow shaft 18 defining a longitudinal axis 16 and having in the proximity of a proximal end two diametrically opposed flat portions.

Figure 2:
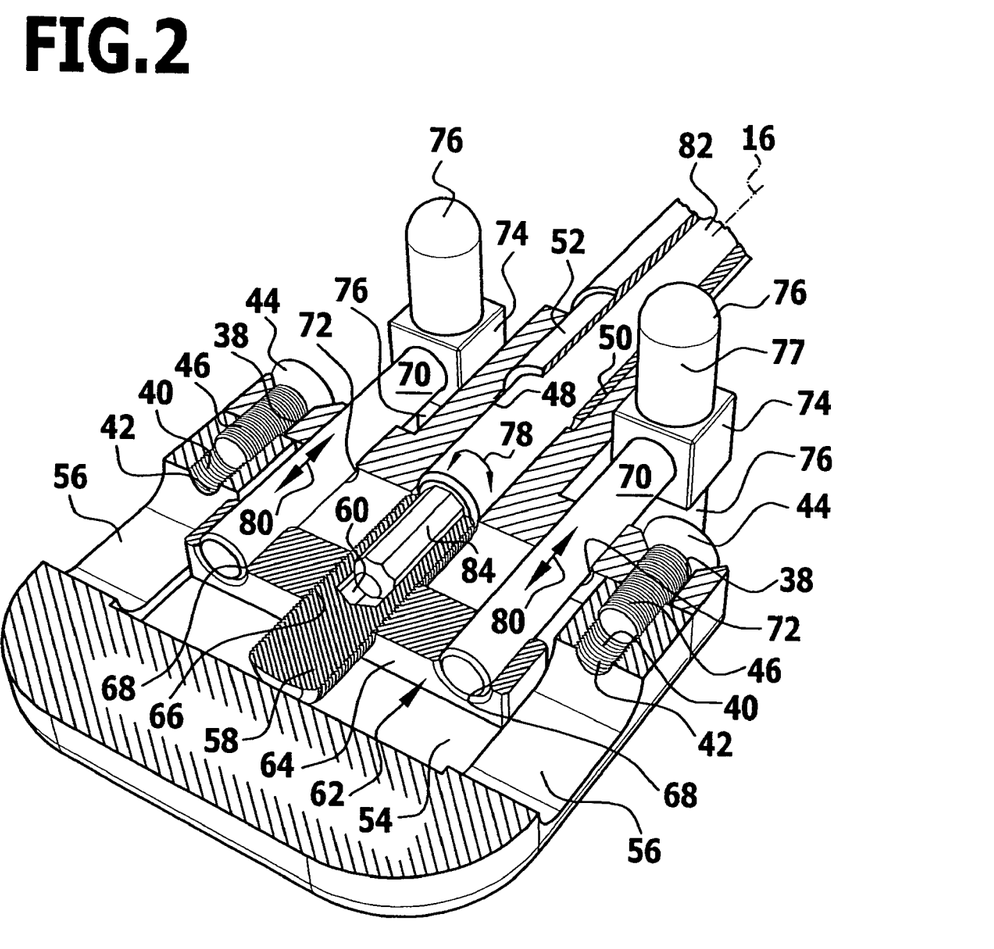
FIG. 2 shows a partially sectional view of a distal end of the instrument from FIG. 1 taken along line 2-2.

Arranged at a distal end of the shaft 18 is an implant body 24 of essentially cuboidal shape, which comprises two bearing surfaces which point in opposite directions and are inclined at an angle of inclination 28 relative to one another. Depending on the purpose for which the guiding instrument 10 is to be used, the angle of inclination 28 may assume values ranging from 0° to 30°. The implant body 24 is of two-part construction and comprises a front part 30 and a rear part 32, the rear part 32 being of essentially T-shaped design. The rear part 32 comprises a middle body 34 which extends substantially parallel to the longitudinal axis 16, and two side bodies 36 which project transversely at a distal end and are flush with a proximal end face of the front part 30. The side bodies 36 are provided with bores 38 which extend parallel to the longitudinal axis 16 and are coaxially aligned with bores 42 on the front part 30 which have an inner thread 40. The rear part is screwed to the front part 30 with two screws 44 having a shaft which is provided with an outer thread 46 corresponding to the inner thread 40 and is insertable through the bores 38.

Coaxially with the longitudinal axis 16, the middle body 34 is provided with a longitudinal bore 48, which tapers in a single step about half-way along the middle body 34 and forms at the proximal end a shaft receptacle 50 into which the distal end 52 of the shaft is introducible and fixable to the middle body 34, for example, by screwing, welding or adhesive bonding.

The front part 30 is provided with an essentially cuboidal recess 54 which is open in proximal direction, but is closed by the rear part 32. Transversely to the longitudinal axis 16, the recess 54 is provided with two windows in the form of elongate holes 56. The recess 54 serves to receive and rotatably mount a threaded spindle 58 arranged coaxially with the longitudinal axis 16 between a delimitation of the recess 54 at a distal side and the distal end of the rear part 32. An inner octagon 60 open in proximal direction and forming a shaft receptacle is formed in the threaded spindle 58. There is mounted in the recess 54 on the threaded spindle 58 a bearing slide 62, which comprises a transverse carrier 64, which extends transversely to the longitudinal axis 16 and is provided with an inner thread 66 extending coaxially with the longitudinal axis 16 and corresponding to the outer thread of the threaded spindle 58. Parallel to the longitudinal axis 16, there are provided on the transverse carrier 64 symmetrically in relation to the longitudinal axis 16 bores 68, in which guide bars 70 are inserted and fixedly connected to the transverse carrier 64. Two guide bores 72, through which the guide bars 70 pass, are provided on the side bodies 36 parallel to the bores 38. Proximal ends of the guide bars 70 terminate in a cube-shaped guide body 74 whose edge length is greater than a diameter of the guide bars 70. Projecting from each guide body 74, transversely to the longitudinal axis 16 and substantially transversely to the bearing surfaces 26 are two stop pins 76 which form stops. Their free ends are rounded off in the shape of a semicircle and their side faces pointing in distal direction form stop surfaces 77.

As a result of rotation of the threaded spindle 58, as symbolized by the arrow 78 in FIG. 2, the bearing slide 62 is moved in a direction parallel to the longitudinal axis 16 in either distal or proximal direction, which is symbolized by the arrows 80 in FIG. 2.

A drive shaft 82 forming a power transmission member is provided for driving the threaded spindle 58. The drive shaft 82 passes through the shaft 18 and is provided at its distal end with an octagon 84 which corresponds to the inner octagon 60 and is insertable from the proximal end into the inner octagon 60 in a positively locked manner. A proximal end of the drive shaft 82 is shaped in the form of a hexagon 86.

Figure 4:
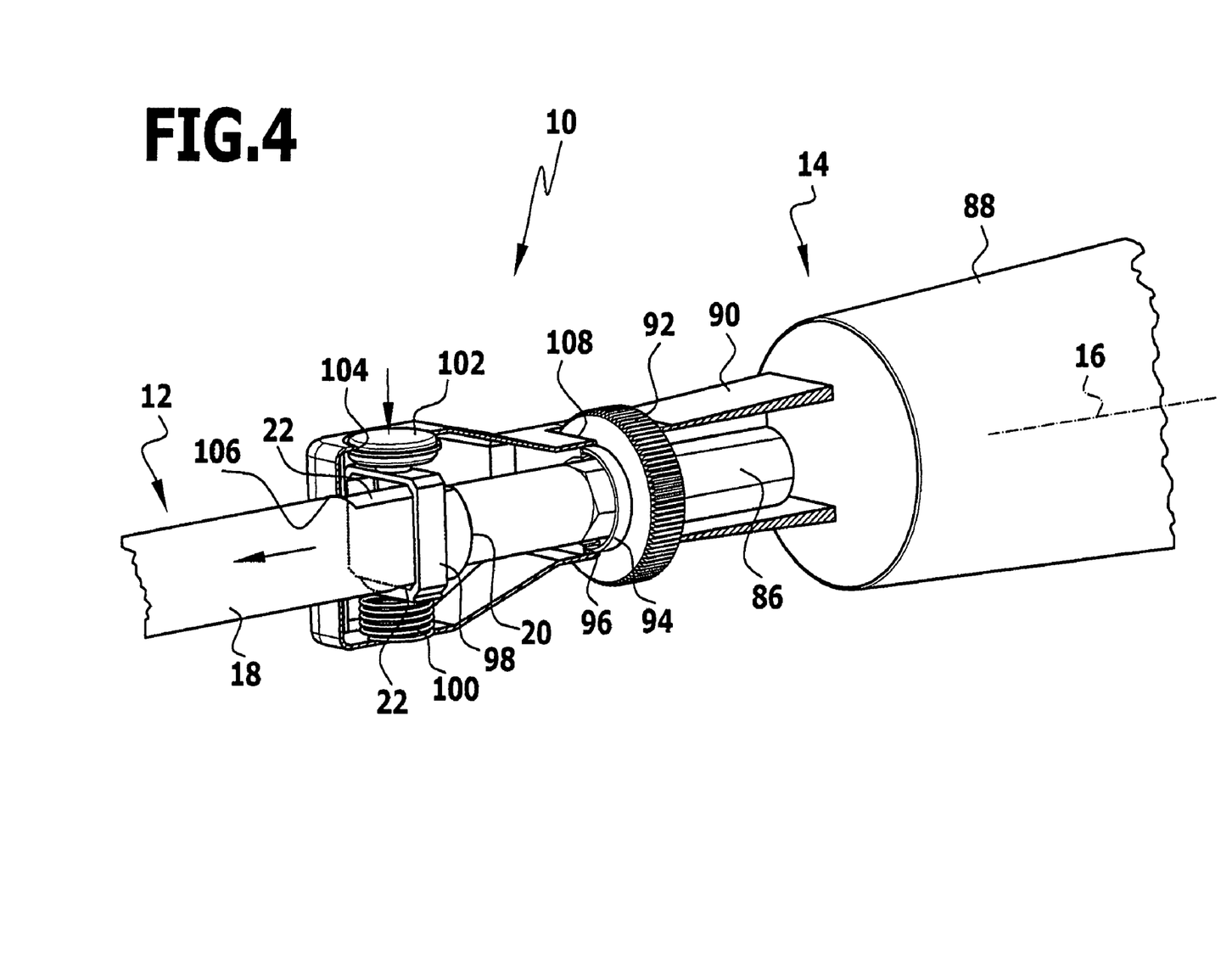
FIG. 4 shows a sectional view taken along line 4-4 in FIG. 1.

The handle part 14 comprises an elongated, ergonomically shaped hand grip 88, adjoining the distal end of which there is a coupling housing 90. A drive wheel 92 forming an actuating member is mounted on the housing 90 for rotation about the longitudinal axis 16. The drive wheel 92 is provided on an outer side thereof with a flat toothing which facilitates actuation of the drive wheel 92. Coaxially with the longitudinal axis 16, the drive wheel 92 is provided with an inner hexagon, which corresponds in design to the hexagon 86, so that the latter is insertable through the drive wheel 92 in a positively locked manner. Furthermore, the drive wheel 92 has at the distal end an annular flange 94 which enters a corresponding annular groove 96 open in proximal direction on the coupling housing 90 and is guided in the annular groove 96, so that the drive wheel 92 is mounted on the coupling housing 90 for rotation about the longitudinal axis 16. The hexagon 86 and the inner hexagon, not shown, of the drive wheel 92 each form a coupling member of a coupling device with which the drive shaft 82 is releasably connectable to the drive wheel 92.

A square frame 98 is mounted for displacement transversely to the longitudinal axis in the region of the distal end of the coupling housing 90, more specifically, it is supported at one side on the housing 90 via a helical spring 100 and is connected on an opposite side to a push button 102 guided in a recess 104 of the coupling housing 90. The frame 98 is pressed by the helical spring 100 in the direction towards the push button 102 which in a normal position bears against the coupling housing 90. The flat portions 22 and the frame 98 form connecting members of a connecting device, more specifically, in the form of a locking connection. The flat portions 22 form locking members in the form of locking recesses, and the frame 98 forms a locking member in the form of a locking latch mounted in a spring-biased manner on the handle part 14.

A circular opening 106 whose diameter is chosen so as to correspond to an outer diameter of the shaft 18 is provided at the distal end on the coupling housing 90. Also provided on the coupling housing 90 are transverse slots 108 through which part of the drive wheel 92 projects from the coupling housing 90.

To connect the shaft part 12 to the handle part 14, the drive shaft 82 projecting at the proximal end from the shaft 18 is first inserted through the opening 106, through the frame 98 and through the drive wheel 92. The proximal end of the shaft 18 is simultaneously inserted through the opening 106 and the frame 98. During the insertion, the frame 98 slides on the end 20 of the shaft 18 and is moved against the spring force of the helical spring 100 in the direction towards the latter. Once the shaft 18 has been inserted into the coupling housing 90 to such an extent that the frame 98 can enter the flat portion 22, the helical spring 100 pushes the frame 98 in the direction towards the shaft 18 and hence also the push button 102 against the coupling housing 90. In this way, the shaft 18 and the drive shaft 82 are axially secured to the handle part 14.

Two longitudinal grooves 110 extending parallel to the longitudinal axis 16 are provided in the bearing surfaces 26 on the implant body 24. A distal end of the longitudinal groove 110 terminates with a distal end of the front part 30, a proximal end of the longitudinal groove 110 terminates with a proximal end of the middle body 34. The longitudinal grooves 110 form guide grooves for a surgical machining tool, for example, a surgical chisel 112.

The guiding instrument 110 may be part of a set of guiding instruments. Such a set may comprise, for example, a handle part 14 and a plurality of shaft parts 12. The shaft parts 12 preferably differ in shape and size of the implant body 24. In particular, the spacings of the bearing surfaces 26 from one another and the angles of inclination 28 differ in these implant bodies 24.

Furthermore, the guiding instrument 10 may also be part of a surgical instrumentarium which, in particular, comprises at least one chisel 112. The chisel 112 preferably comprises a hollow shaft 116 which, after the handle part 14 is released from the shaft part 12, can be pushed in distal direction over the shaft 18. As shown, for example, in FIG. 3, a two-part cutting edge 118 is arranged at a distal end of the shaft 116, thereby forming a so-called double chisel. The cutting edge 118 is designed so that its width corresponds to a width of the longitudinal grooves 110, and, in addition, a spacing of the two cutting edge halves forming the cutting edge 118 from one another corresponds to a spacing of groove bottoms 120 of the longitudinal grooves 110 transversely to the longitudinal axis 16. Furthermore, the chisel 112 may have a blade guard 122 mounted on the shaft 116. In a normal position, the blade guard 122 is held in a spring-biased manner over the cutting edge 118 and can be retracted against the force of a spring, not shown, in proximal direction.

Use of the instrumentarium 114 will now be explained in greater detail hereinbelow.

To prepare the guiding instrument 10, the shaft part 12 is connected in the above-described manner to the handle part 14. By turning the drive wheel 92, the drive shaft 82 is made to rotate, more specifically, for such a time until the bearing slide 62 is brought into its most distal position and the guide bodies 74 bear against the side bodies 36. The stop pins 76 now assume their most distal position in relation to the shaft 18.

Figure 3:
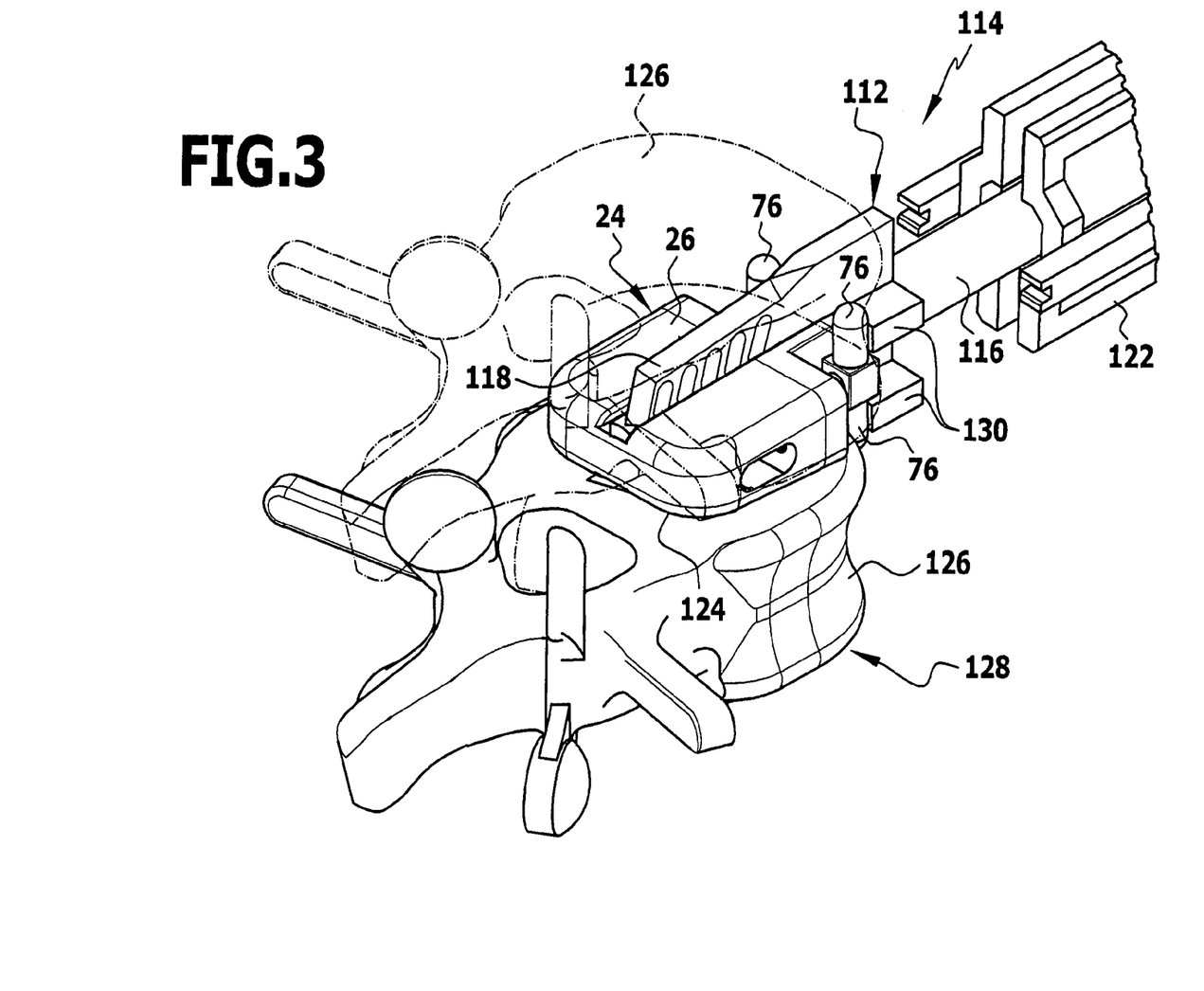
FIG. 3 shows a schematic illustration during the machining of a vertebral body with an instrumentarium according to the invention.

The implant body 24 is introduced through an access into the body of a human being or an animal and into an intervertebral space 124 between adjacent vertebral bodies 126 of a vertebral column 128. The shaft part 12 is selected such that the implant body 24 will correspond to an implant to be implanted later into the intervertebral space 24 insofar as the spacing of the bearing surfaces 26 and an inclination of the same relative to one another match. The implant body 24 is introduced into the intervertebral space 124 until the stop pins 76 projecting over the bearing surfaces 26 bear against the vertebral bodies 126. With the assistance of X-ray monitoring, for example, an operator can now determine whether the implant body 24 has been advanced far enough into the intervertebral space 124. If this is not the case, the drive shaft 82 is then made to rotate again with the drive wheel 92, but in the direction opposite to that for preparing the guiding instrument 10, in order to move the guide bodies 74 away from the side bodies 36. The stop pins 76 are thus moved in proximal direction and away from the implant body 24, more specifically, precisely to such an extent that the implant body 24 can be inserted further still into the intervertebral space 124. After adjusting the stop pins 76, the implant body 24 is advanced further into the intervertebral space 124 until the stop pins 76 bear again against the vertebral bodies 126. This adjusting procedure is continued until the implant body 24 assumes the desired position in the intervertebral space 124.

To form a recess in surfaces of the vertebral bodies 126, in particular, for receiving, for example, a fin-like projection on the intervertebral implant to be inserted later, the handle part 14 is separated from the shaft part 12. This is done by pressing the push button 102, whereby the helical spring 100 is compressed somewhat, with the result that the frame 98 releases the flat portion 22, and the shaft 18 can be pulled in distal direction out of the coupling housing 90. The chisel 112 with the cutting edge 118 of desired shape and size is then pushed with its shaft 116 over the shaft 18. Projections 130 extending transversely on the cutting edge 118 form stops which prevent the cutting edge 118 from being able to be advanced too far in distal direction. It is designed so as to be able to bear against the stop pins 76 or, alternatively, also against the proximal end of the middle body 34.

Owing to the guiding instrument 10 and the stop pins 76 movably mounted thereon, the chisel 112 is prevented from being able to be introduced too deeply into the intervertebral space 124, which would result in an unnecessary partial resection of the vertebral bodies 126 and, in the worst case, even injury to the nerves running in the vertebral canal.

Once the grooves are formed in the desired manner in the vertebral bodies 126, the chisel 112 is first withdrawn from the shaft part 12, the handle part 14 is then connected to the shaft part 12 again, and the guiding instrument 10 is removed from the body.

The guiding instrument 10 and the entire instrumentarium 114 are made from materials that can be steam-sterilized. The entire guiding instrument 10, except for the hand grip 88, is preferably made from an instrument steel.

Although the invention is illustrated and described herein with reference to specific embodiments, the invention is not intended to be limited to the details shown. Rather, various modifications may be made in the details within the scope and range of equivalents of the claims and without departing from the invention.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed is:

1. A surgical guiding instrument for a surgical machining tool, with an implant body for insertion into an intervertebral space between adjacent vertebral bodies of a vertebral column of a human being or an animal, the guiding instrument comprising a shaft and a stop device for delimiting a depth of insertion of the implant body into the intervertebral space, the shaft having a distal end and a proximal end, the implant body being arranged at the distal end of the shaft and defining two bearing surfaces positionable against the adjacent vertebral bodies, the stop device having at least one stop movably mounted at the distal end of the shaft or on the implant body, the stop having a stop surface pointing in a distal direction transversely or substantially transversely to at least one of the bearing surfaces, wherein the stop device comprises an actuating member arranged at the proximal end or in the region of the proximal end of the shaft and a power transmission member mounted on the shaft, and the actuating member, the power transmission member and the at least one stop are arranged and designed to interact in such a way that the at least one stop is movable in proximal and/or distal direction by actuating the actuating member, the actuating member being releasably connectable to the power transmission member.

2. The guiding instrument in accordance with claim 1, wherein a coupling device is provided for connecting the power transmission member to the actuating member, a first coupling member and a second coupling member engageable in a coupling position with the first coupling member are provided, the first coupling member is arranged on the actuating member, and the second coupling member is arranged on the power transmission member.

3. The guiding instrument in accordance with claim 2, wherein one of the two coupling members is a member of polygonal cross section having outer planar sides or a member of generally polygonal cross section having outer rounded sides and edges, and the other one of the two coupling members is a corresponding member of polygonal cross section having inner planar sides or a corresponding member of generally polygonal cross section having inner rounded sides and edges.

4. The guiding instrument in accordance with claim 1, wherein a handle part is provided at the proximal end of the shaft.

5. The guiding instrument in accordance with claim 4, wherein the handle part is releasably connectable to the shaft.

6. The guiding instrument in accordance with claim 5, wherein a connecting device is provided for connecting the shaft to the handle part, a first connecting member and a second connecting member engageable in a connecting position with the first connecting member are provided, the first connecting member is arranged on the shaft, and the second connecting member is arranged on the handle part.

7. The guiding instrument in accordance with claim 6, wherein one of the two connecting members is a member of polygonal cross section having outer planar sides or a member of generally polygonal cross section having outer rounded sides and edges, and the other one of the two connecting members is a corresponding member of polygonal cross section having inner planar sides or a corresponding member of generally polygonal cross section having inner rounded sides and edges.

8. The guiding instrument in accordance with claim 7, wherein the member of polygonal cross section having outer planar sides forms a short shaft section of the shaft, and the member of polygonal cross section having inner planar sides is arranged on the handle part.

9. The guiding instrument in accordance with claim 6, wherein the connecting device is designed in the form of a locking connection, the two connecting members are designed in the form of locking members which in a lock position are engaged, and the two locking members are arranged so that they are moveable relative to one another during the transition from the lock position to a release position in which they are disengaged, and vice versa.

10. The guiding instrument in accordance with claim 9, wherein one of the locking members is designed in the form of a locking recess arranged on the shaft, and the other locking member is a spring-biased locking latch mounted on the handle part.

11. The guiding instrument in accordance with claim 10, wherein the locking latch is mounted for movement in a direction transverse to a longitudinal axis of the shaft.

12. The guiding instrument in accordance with claim 4, wherein the actuating member is arranged on the handle part.

13. The guiding instrument in accordance with claim 1, wherein the power transmission member is a drive shaft mounted for rotation on the shaft.

14. The guiding instrument in accordance with claim 1, wherein the actuating member is a drive wheel mounted for rotation about a longitudinal axis of the shaft.

15. The guiding instrument in accordance with claim 1, wherein a chisel guide is provided on the implant body.

16. The guiding instrument in accordance with claim 15, wherein the chisel guide comprises at least one guide groove, and the at least one guide groove is arranged so as to run in one of the two bearing surfaces parallel or substantially parallel to a longitudinal axis of the shaft.

17. The guiding instrument in accordance with claim 15, wherein at least part of the chisel guide projects at the proximal end from the implant body.

18. The guiding instrument in accordance with claim 15, wherein the chisel guide respectively comprises a longitudinal groove on each bearing surface.

19. The guiding instrument in accordance with claim 1, wherein the at least one stop is mounted on the implant body for displacement parallel or substantially parallel to a longitudinal axis of the shaft.

20. The guiding instrument in accordance with claim 1, wherein a drive mechanism is provided for moving the at least one stop, and the drive mechanism is arranged on the shaft or on the implant body and designed so that the at least one stop is moveable as a result of a rotational movement of the power transmission member.

21. The guiding instrument in accordance with claim 20, wherein the drive mechanism comprises a spindle drive for moving the at least one stop.

22. The guiding instrument in accordance with claim 21, wherein the spindle drive comprises a bearing slide mounted on the implant body for displacement parallel or substantially parallel to the longitudinal axis and carrying the at least one stop, and a threaded spindle mounted for rotation about an axis of rotation extending parallel or substantially parallel to the longitudinal axis and having an outer thread corresponding to an inner thread provided on the bearing slide, and the threaded spindle is connected or connectable to the power transmission member.

23. The guiding instrument in accordance with claim 22, wherein the at least one stop projects transversely to the longitudinal axis from a proximal end of the bearing slide.

24. The guiding instrument in accordance with claim 20, wherein the drive mechanism comprises a power transmission member receptacle with which a distal end of the power transmission member engages in a positively locked manner.

25. The guiding instrument in accordance with claim 1, wherein the at least one stop is mounted so as to project in proximal direction from the implant body.

26. The guiding instrument in accordance with claim 1, wherein two or four stops are provided.

27. The guiding instrument in accordance with claim 1, wherein the instrument is of mirror-symmetrical design in relation to a mirror plane containing a longitudinal axis of the shaft.

28. A set of surgical guiding instruments for a surgical machining tool, with an implant body for insertion into an intervertebral space between adjacent vertebral bodies of a vertebral column of a human being or an animal, each surgical guiding instrument comprising a shaft and with a stop device for delimiting a depth of insertion of the implant body into the intervertebral space, the shaft having a distal end and a proximal end, the implant body being arranged at the distal end of the shaft and defining two bearing surfaces positionable against the adjacent vertebral bodies, wherein the set comprises two or more guiding instruments for a surgical machining tool, with an implant body for insertion into an intervertebral space between adjacent vertebral bodies of the vertebral column of a human being or an animal, each of said two or more guiding instruments comprising a shaft and with a stop device for delimiting a depth of insertion of the implant body into the intervertebral space, the shaft having a distal end and a proximal end, the implant body being arranged at the distal end of the shaft and defining two bearing surfaces positionable against the adjacent vertebral bodies, the stop device having at least one stop movably mounted at the distal end of the shaft or on the implant body, the stop having a stop surface pointing in distal direction transversely or substantially transversely to at least one of the bearing surfaces, wherein the stop device comprises an actuating member arranged at the proximal end or in the region of the proximal end of the shaft and a power transmission member mounted on the shaft, the actuating member being releasably connectable to the power transmission member and the actuating member, the power transmission member and the at least one stop are arranged and designed to interact in such a way that the at least one stop is movable in proximal and/or distal direction by actuating the actuating member, and wherein the two or more guiding instruments comprise implant bodies of different size and/or different shape.

29. Surgical instrumentarium comprising at least one surgical machining tool and at least one surgical guiding instrument for the at least one surgical machining tool, with an implant body for insertion into an intervertebral space between adjacent vertebral bodies of a vertebral column of a human being or an animal, with the at least one surgical guiding instrument comprising a shaft and a stop device for delimiting a depth of insertion of the guiding instrument into the intervertebral space, the shaft having a distal end and a proximal end, the implant body being arranged at the distal end of the shaft and defining two bearing surfaces positionable against the adjacent vertebral bodies, the stop device having at least one stop movably mounted at the distal end of the shaft or on the implant body, the stop having a stop surface pointing in distal direction transversely or substantially transversely to at least one of the bearing surfaces, wherein the at least one surgical guiding instrument is an instrument for a surgical machining tool with an implant body for insertion into an intervertebral space between adjacent vertebral bodies of the vertebral column of a human being or an animal, with a shaft and with a stop device for delimiting a depth of insertion of the implant body into the intervertebral space, the shaft having a distal end and a proximal end, the implant body being arranged at the distal end of the shaft and defining two bearing surfaces positionable against the adjacent vertebral bodies, the stop device having at least one stop movably mounted at the distal end of the shaft or on the implant body, the stop having a stop surface pointing in distal direction transversely or substantially transversely to at least one of the bearing surfaces, wherein the stop device comprises an actuating member arranged at the proximal end or in the region of the proximal end of the shaft and a power transmission member mounted on the shaft, the actuating member being releasably connectable to the power transmission member and the actuating member, the power transmission member and the at least one stop are arranged and designed to interact in such a way that the at least one stop is movable in proximal and/or distal direction by actuating the actuating member.

30. The surgical instrumentarium in accordance with claim 29, wherein the at least one machining tool is a single or a double chisel.

31. The surgical instrumentarium in accordance with claim 29, wherein the at least one machining tool comprises a hollow tool shaft, at the distal end of which at least one tool cutting edge is arranged, and the shaft of the guiding instrument is introducible into the tool shaft.

32. Surgical instrumentarium comprising at least one surgical machining tool and at least one surgical guiding instrument for the at least one surgical machining tool, with an implant body for insertion into an intervertebral space between adjacent vertebral bodies of a vertebral column of a human being or an animal, with the at least one surgical guiding instrument comprising a shaft and a stop device for delimiting a depth of insertion of the at least one surgical guiding instrument into the intervertebral space, the shaft having a distal end and a proximal end, the implant body being arranged at the distal end of the shaft and defining two bearing surfaces positionabie against the adjacent vertebral bodies, the stop device having at least one stop movably mounted at the distal end of the shaft or on the implant body, the stop having a stop surface pointing in distal direction transversely or substantially transversely to at least one of the bearing surfaces, wherein the at least one surgical guiding instrument is a set of surgical guiding instruments for a surgical machining tool, with an implant body for insertion into an intervertebral space between adjacent vertebral bodies of the vertebral column of a human being or an animal, each of said set of surgical guiding instruments comprising a shaft and a stop device for delimiting a depth of insertion of the implant body into the intervertebral space, the shaft having a distal end and a proximal end, the implant body being arranged at the distal end of the shaft and defining two bearing surfaces positionable against the adjacent vertebral bodies, wherein the set comprises two or more guiding instruments for a surgical machining tool with an implant body for insertion into an intervertebral space between adjacent vertebral bodies of the vertebral column of a human being or an animal, each of said two or more guiding instruments comprising a shaft and a stop device for delimiting a depth of insertion of the implant body into the intervertebral space, the shaft having a distal end and a proximal end, the implant body being arranged at the distal end of the shaft and defining two bearing surfaces positionable against the adjacent vertebral bodies, the stop device having at least one stop movably mounted at the distal end of the shaft or on the implant body, the stop having a stop surface pointing in distal direction transversely or substantially transversely to at least one of the bearing surfaces, wherein the stop device comprises an actuating member arranged at the proximal end or in the region of the proximal end of the shaft and a power transmission member mounted on the shaft, the actuating member being releasably connectable to the power transmission member and the actuating member, the power transmission member and the at least one stop are arranged and designed to interact in such a way that the at least one stop is movable in proximal and/or distal direction by actuating the actuating member, and wherein the two or more guiding instruments comprise implant bodies of different size and/or different shape.

33. A surgical instrument for use in inserting an implant body into an intervertebral space of a human being or an animal, the implant body having two bearing surfaces positionable against adjacent vertebral bodies, the instrument comprising a shaft and a stop device for delimiting a depth of insertion of the implant body into the intervertebral space, the shaft having a distal end and a proximal end, the distal end configured to receive the implant body, the stop device having at least one stop movably mounted at the distal end of the shaft, the at least one stop having a stop surface pointing in a distal direction substantially transversely to the shaft, wherein the stop device comprises an actuating member arranged in a proximal region of the end of the shaft and a power transmission member mounted on the shaft, and the actuating member, the power transmission member and the at least one stop are arranged such that the at least one stop is movable by actuating the actuating member, wherein a drive mechanism is provided for moving the at least one stop, and the drive mechanism is arranged on the shaft so that the at least one stop is moveable as a result of a rotational movement of the power transmission member.

34. The instrument in accordance with claim 33, wherein the actuating member is releasably connectable to the power transmission member.

35. The instrument in accordance with claim 34, further comprising a coupling device provided for connecting the power transmission member to the actuating member, the coupling device having a first coupling member and a second coupling member engageable in a coupling position with the first coupling member, wherein the first coupling member is arranged on the actuating member, and the second coupling member is arranged on the power transmission member.

36. The instrument in accordance with claim 35, wherein one of the two coupling members has a polygonal cross section having outer planar sides or a generally polygonal cross section having outer rounded sides and edges, and the other one of the two coupling members is a corresponding member of polygonal cross section having inner planar sides or a corresponding member of generally polygonal cross section having inner rounded sides and edges.

37. The instrument in accordance with claim 33, further comprising a handle part at the proximal end of the shaft.

38. The instrument in accordance with claim 37, wherein the handle part is releasably connectable to the shaft.

39. The instrument in accordance with claim 38, further comprising a connecting device provided for connecting the shaft to the handle part, the connecting device having a first connecting member and a second connecting member engageable in a connecting position with the first connecting member, wherein the first connecting member is arranged on the shaft, and the second connecting member is arranged on the handle part.

40. The instrument in accordance with claim 39, wherein one of the two connecting members has a polygonal cross section having outer planar sides or a generally polygonal cross section having outer rounded sides and edges, and the other one of the two connecting members is a corresponding member of polygonal cross section having inner planar sides or a corresponding member of generally polygonal cross section having inner rounded sides and edges.

41. The instrument in accordance with claim 40, wherein the member of polygonal cross section having outer planar sides forms a short shaft section of the shaft, and the member of polygonal cross section having inner planar sides is arranged on the handle part.

42. The instrument in accordance with claim 39, wherein the connecting device is designed in the form of a locking connection, the two connecting members are designed in the form of locking members which in a lock position are engaged, and the two locking members are arranged so that they are moveable relative to one another during the transition from the lock position to a release position in which they are disengaged.

43. The instrument in accordance with claim 42, wherein one of the locking members has a locking recess arranged on the shaft, and the other locking member is a spring-biased locking latch mounted on the handle part.

44. The instrument in accordance with claim 43, wherein the locking latch is mounted for movement in a direction transverse to the longitudinal axis of the shaft.

45. The instrument in accordance with claim 37, wherein the actuating member is arranged on the handle part.

46. The instrument in accordance with claim 33, wherein the power transmission member is a drive shaft mounted for rotation on the shaft.

47. The instrument in accordance with claim 33, wherein the actuating member is a drive wheel mounted for rotation about a longitudinal axis of the shaft.

48. The instrument in accordance with claim 33, wherein the drive mechanism comprises a spindle drive for moving the at least one stop.

49. The instrument in accordance with claim 33, wherein the drive mechanism comprises a power transmission member receptacle with which a distal end of the power transmission member engages in a positively locked manner.

* * * * *

UNITED STATES PATENT AND TRADEMARK OFFICE
CERTIFICATE OF CORRECTION

PATENT NO. : 7,749,271 B2  
APPLICATION NO. : 11/508461  
DATED : July 6, 2010  
INVENTOR(S) : Kay Fischer and Robert Schultz It is certified that error appears in the above-identified patent and that said Letters Patent is hereby corrected as shown below:

Title Page, Item (73) Assignee:

Please enter a (.) after "Co"

To read

--(73) Assignee: Aesculap AG & Co. KG--.

Signed and Sealed this
Eleventh Day of January, 2011

David J. Kappos
*Director of the United States Patent and Trademark Office*